(12) United States Patent
Arrowsmith

(10) Patent No.: US 7,044,604 B1
(45) Date of Patent: May 16, 2006

(54) METHOD FOR DETERMINING THE POWER OF AN INTRAOCULAR LENS USED FOR THE TREATMENT OF MYOPIA

(76) Inventor: Peter N. Arrowsmith, 210 25th Ave. North, Suite 900, Nashville, TN (US) 37203

( * ) Notice: Subject to any disclaimer, the term of this patent is extended or adjusted under 35 U.S.C. 154(b) by 456 days.

(21) Appl. No.: 10/660,248

(22) Filed: Sep. 11, 2003

Related U.S. Application Data

(63) Continuation-in-part of application No. 09/903,385, filed on Jul. 11, 2001, now Pat. No. 6,626,538.

(51) Int. Cl.
 *A61B 3/00* (2006.01)
(52) U.S. Cl. ............... 351/246; 623/4.1; 623/6.11
(58) Field of Classification Search ............... 351/200, 351/246; 623/4.1, 6.11
See application file for complete search history.

(56) References Cited

U.S. PATENT DOCUMENTS

| | | | |
|---|---|---|---|
| 5,116,115 A | 5/1992 | Lange et al. ............... 351/212 |
| 5,728,155 A | 3/1998 | Anello ........................... 623/6 |
| 5,864,378 A | 1/1999 | Portney ....................... 351/160 |
| 5,964,802 A | 10/1999 | Anello et al. ................... 623/6 |
| 5,984,962 A | 11/1999 | Anello et al. ................... 623/6 |
| 6,024,447 A | 2/2000 | Portney ....................... 351/160 |
| 6,126,286 A | 10/2000 | Portney ....................... 351/160 |
| 6,419,359 B1 | 7/2002 | Edwards ...................... 351/177 |
| 6,450,642 B1 | 9/2002 | Jethmalani et al. ......... 351/219 |
| 6,626,538 B1 | 9/2003 | Arrowsmith ................ 351/246 |
| 6,634,751 B1 * | 10/2003 | Turner et al. ............... 351/212 |
| 6,824,266 B1 * | 11/2004 | Jethmalani et al. ......... 623/6.11 |
| 2004/0054358 A1 * | 3/2004 | Cox et al. ....................... 606/5 |
| 2005/0225721 A1 * | 10/2005 | Harris et al. ................ 351/200 |

OTHER PUBLICATIONS

S. Karger et al, A Comparative Study of Eight Intraocular Lens Calculation Formulas, Ophthalmologica, 1991, 148-153, vol. 203, U.S.A.

Kenneth J. Hoffer, M.D., The Hoffer Q formula: A Comparison of Theoretic and Regression Formulas, J Cataract Refract Surg, Nov. 1993, 700-712, vol. 19, U.S.A.

Thomas Olsen, M.D. et al, Theoretical Versus SRK I and SRK II Calculation of Intraocular Lens Power, J Cataract Refract Surg, Mar. 1990, 217-225, vol. 16, U.S.A.

(Continued)

*Primary Examiner*—Ali Imam
*Assistant Examiner*—John R Sanders
(74) *Attorney, Agent, or Firm*—Waddey & Patterson; Mark J. Patterson

(57) ABSTRACT

A method of deriving a prediction model and calculating a predicted lens power to provide a desired post-operative spherical equivalent to correct myopia in a phakic eye of a patient using an intraocular lens includes measuring and determining the predictive significance of certain pre-operative characteristics of the eye, including cycloplegic and manifest spherical equivalent, vertex distance, anterior chamber depth, axial length, and keratometry. The prediction model is derived using multiple regression analysis on the pre-operative and post operative data. Measured data corresponding to a particular patient is used in the lens power prediction model to calculate the predicted lens power for implantation in the patient.

1 Claim, 11 Drawing Sheets

OTHER PUBLICATIONS

Donald R. Sanders, M.D.,Ph.D. et al, Comparison of the SRK/T Formula and Other Theoretical and Regression Formulas, May 1990, 341-346, vol. 16, U.S.A.

Milton Katz et al, The Human Eye as an Optical System, Clinical Ophthalmology, 1998, 1-56, vol. 1, U.S.A.

Jack T. Holladay, M.D., Refractive Power Calculations for Intraocular Lenses in the Phakic Eye, American Journal of Ophthalmology, Jul. 1993, 63-66, vol. 116, U.S.A.

Jack T. Holladay et al, Improving the Predictability of Intraocular Lens Power Calculations, Arch Ophthalmol, Apr. 1986, 539-541, vol. 104, U.S.A.

G.L. Van Der Heijde, Some Optical Aspects of Implantation of an IOL in a Myopic Eye, Eur J Implant Ref Surg, Dec. 1989, 245-248, vol. 1, Amsterdam, The Netherlands.

Paul U. Fechner, M.D., et al, The Correction of Myopia by Lens Implantation Into Phakic Eyes, American Journal of Ophthalmology, Jun. 1989, 659-663, vol. 107 No. 6, U.S.A.

Donald R. Sanders, M.D., Ph.D. et al, A-Scan Biometry and IOL Implant Power Calculations, American Academy of Ophthalmology Focal Points, Dec. 1995, 1-14, vol. 13 No. 10, U.S.A.

Paul U. Fechner, M.D. et al, Worst-Fechner Biconcave Minus Power Phakic Iris-Claw Lens, Journal of Refractive Surgery, Mar./Apr. 1999, 93-105, vol. 15, U.S.A.

John Retzlaff, M.D. et al, A Manual of Implant Power Calculation, SRK Formula, 1-41, U.S.A.

Jack T. Holladay, MD, MSEE, Standardizing Constants for Ultrasonic Biometry, Keratometry, and Intraocular Lens Power Calculations, J Cataract Refractive Surgery, Nov. 1997, 1356-1370, vol. 23, U.S.A.

Kristian Naeser, MD, Intraocular Lens Power Formula Based on Vergence Calculation and Lens Design, J Cataract Refractive Surgery, Oct. 1997, 1200-1207, vol. 23, U.S.A.

Thomas Olsen, M.D. et al, Intraocular Lens Power Calculation With an Improved Anterior Chamber Depth Prediction Algorithm, J Cataract Refractive Surgery, May 1995, 313-319, vol. 21, U.S.A.

Jack T. Holladay, M.D. et al, A Three-Part System For Refining Intraocular Lens Power Calculations, J Cataract Refractive Surgery, Jan. 1988, 17-24, vol. 14, U.S.A.

* cited by examiner

Summary of Fit

| | |
|---|---|
| RSquare | 0.973369 |
| RSquare Adj | 0.973309 |
| Root Mean Square Error | 0.51155 |
| Mean of Response | -12.7978 |
| Observations (or Sum Wgts) | 450 |

METHOD FOR DETERMINING THE POWER OF AN INTRAOCULAR LENS USED FOR THE TREATMENT OF MYOPIA

This application claims benefit of, and is a continuation-in-part of, U.S. patent application Ser. No. 09/903,385 filed Jul. 11, 2001, now U.S. Pat. No. 6,626,538 entitled "METHOD FOR DETERMINING THE POWER OF AN INTRAOCULAR LENS USED FOR THE TREATMENT OF MYOPIA.

A portion of the disclosure of this patent document contains material that is subject to copyright protection. The copyright owner has no objection to the facsimile reproduction by anyone of the patent document or the patent disclosure, as it appears in the Patent and Trademark office patent file or records, but otherwise reserves all copyright rights whatsoever.

BACKGROUND OF THE INVENTION

The present invention relates generally to intraocular lenses used for the treatment of myopia.

More particularly, this invention pertains to methods of determining the power of a phakic intraocular lens based on the needs of a specific patient.

Refractive error is a mismatch between the power of the eye's optical components (primarily the cornea and lens) and the axial length of the eye, such that when the eye is in its relaxed state the retinal image of a distant object will be blurred. Myopia (sometimes called nearsightedness) is a term used to describe faulty vision caused by an error of refraction in which rays of light entering the eye are brought into focus in front of the retina, usually as a result of the eyeball being too long from front to back. Eyeglasses and contact lenses are typically used to correct myopia.

The term phakic is applied to characterize an eye in which the natural ocular lens is still present. Conversely, an aphakic eye is one from which the natural ocular lens has been removed. A phakic eye is considered a dynamic or active eye because the living natural lens is subject to change over time, while an aphakic eye is considered a static eye because the natural lens has been removed.

Phakic intraocular lenses ("IOLs") have been shown to be effective as a surgical correction for myopia. There appears to be no other suitable surgical alternative in cases of extremely high myopia or thin cornea. Phakic IOLs are now finding place in the surgical treatment for mid-range myopia and hyperopia as well. However, if the phakic IOL is to compete with LASIK (Laser Assisted in-Situ Keratomileusis) for mid range refractive error, careful attention must be paid to the refractive outcome. A LASIK patient slightly under or over corrected may undergo an enhancement procedure with little risk or loss of time. Lens exchange, on the other hand, probably involves more risk and presents a less suitable alternative. A precise power prediction for the IOL is, therefore, most important. Two theoretical phakic IOL formulas have been published. These formulas include characteristics that differ in important ways from aphakic IOL formulas.

Anterior chamber phakic IOLs were introduced by Strampelli and Barraquer in the 1950s. During the ensuing 15 years, over half of the 450 implanted lenses were explanted because of corneal endothelial damage or other complications. Phakic IOLs hold refractive advantages to LASIK for the treatment of high myopia especially when corneal thickness is a limiting factor. Despite early complications, the obvious clinical importance of this technique has spurred renewed interest.

Phakic IOLs include 3 basic designs: (1) posterior chamber lenses called ICLs (intraocular contact lenses) (sometimes referred to as Fyodorov or Staar Collamer lenses); (2) a variety of anterior chamber angle-supported lenses after the Kellman four point Multiflex IOL (Nuvita by Bausch and Lomb, Domilens or ZB5M by Chiron, and ZSAL-4 by Morcher GmbH); and (3) iris-stromal-supported lenses after Prof Jan Worst of the Netherlands (the Artisan lens from OPHTEC).

Fyorodov was the first to introduce the posterior chamber silicone ICL for the correction of myopia. He and his colleagues implanted over 1000 silicon posterior chamber intraocular lenses in phakic eyes. Brauweiler and his co-authors reported an 81.9% rate of secondary cataract formation at 2 years post-implantation.

Subsequent studies with the Staar Collamer posterior chamber ICL have indicated more favorable results. However, complications continue to include narrow angle glaucoma, retinal detachment, and cataract. Trindade utilized ultrasound biomicroscopic imaging to evaluate posterior chamber phakic ICLs. There was a consistent reduction in anterior chamber depth and localized narrowing of angle opening. Pesando and co-authors reported acute angle closure glaucoma to be 13.33% with the collamer posterior chamber phakic lens. Other problems including IOL-iris touch, IOL-crystalline lens touch, and anterior chamber shallowing raise concerns of pigmentary dispersion, cataractogenesis, as well as narrow angle glaucoma following posterior phakic intraocular lens implantation.

Modifications of the Kellman Multiflex, phakic angle supported lens have shown reduced rates of complications compared to phakic posterior chamber lenses. The Baikoff ZB lens was associated, however, with high endothelial cell loss. Subsequently, the ZB5M lens provided for 0.6 mm greater corneal clearance, and clinical studies have shown a reduced long-term endothelial cell loss. A fourth generation modification, the ZSAL-4 lens from Morcher GmbH has 19 degree haptic angulation to reduce iris contact and a 5 mm optic to reduce glare. Transient low grade iritis, pupil ovalization from iris entrapment by haptics, and lens rotation remain problems. The mean endothelial cell loss was 4.8% at 24 months. Alio and co-authors found a potential risk of nuclear cataract after phakic IOL implantation in patients over 40 years of age and in those with axial myopia greater than 30 mm. However, cataract development is known to be 4 times more frequent in those with high myopia than in the general population. Furthermore, in eyes with axial length greater than 29.0 mm, the incidence is significant at age 50 years.

Fechner introduced the iris-claw anterior chamber lens conceived by Professor Jan Worst of the Netherlands. The design of the lens is intended: (a) to avoid AC angle contact; (b) to limit likelihood of endothelial contact by low profile design; (c) to provide adequate clearance of the implant from the iris and crystalline lens; and (d) to provide stability by fixation to mid-stromal iris.

U.S. clinical investigation, phase 1 and 2 and interim phase 3, for the Artisan myopia lens indicated an initial complication rate of 39% on initial visit to 10% on visit four, to 0% on visit seven. The Artisan lens offers an option for the correction of high degrees of myopia.

Phakic intraocular lenses have proven optically effective. However, the post-operative need for an over-correction with contact lenses or spectacles is more common with phakic IOLs as compared to LASIK. For example, Zaldivar, using the Starr Collamer Posterior Chamber I Lens reported a mean post-operative spherical equivalent refraction of −0.78 +/−0.87 (range of +1.36 to −3.50 diopters). The conclusion was that improvements in phakic IOL formulas are needed to improve the predictability of refractive outcome. Refractive results with the Artisan lens have been better. Trial findings at 6 months indicated manifest spherical equivalent to be within +/−0.5 D of predicted, and 78% within +/−1.00 D predicted.

Modern intraocular lens power formulas were derived from the optical considerations outlined by Gullstrand in 1909. Fyodorov developed an aphakic IOL power formula in 1967 that was revised and published in 1975. Binkhorst developed a theoretical formula and published a calculation manual in 1981. In the prior art, calculations of appropriate IOL power are based on pre-operative measurements of corneal power, axial length, and estimated post-operative pseudophakic anterior chamber depth (ACD). However, as noted above, these prior art formulas vary in predictive value, particularly at the extremes of axial length. Error is uncontrollably introduced in clinical measurement and the effect of axial length and corneal curvature measurement error has been studied and appreciated clinically. However, the post-operative anterior chamber depth estimation has not been subject to precise clinical estimation for a variety of reasons, and the prediction of ACD may account for 20–40% of the total refractive prediction error. Applanation ultrasound biometry has been the standard for the estimation of axial length and ACD. Recently, ACD estimation using dual-beam partial coherent interferometry has been reported.

A linear multiple-regression model was derived to predict the anterior chamber depth. PCI data when applied to the Holladay and SRK/T formulae, yielded a mean average error (MAE) of 0.44 diopter (D) compared to 0.56 D and 0.57 D respectively when US biometry ACD data was applied. Short eyes tend to have shallow ACDs and long eyes tend to have deep ACDs after surgery. To compensate for error, "fudge" factors were applied to theoretical formulas. Factors that have been introduced to improve the IOL power calculation include the A constant (SRK), the surgeon factor, and the anterior chamber depth (ACD) factor. Dealing with variances introduced from variable post-operative ACD has proven to be challenging. When the pre-operative ACD is analyzed by multiple regression in combination with corneal height and axial length, this variable has been shown in some applications to be predictive for both anterior and posterior chamber lenses. The inclusion of lens thickness in the algorithm did reach statistical significance in the prediction of ACD.

The continuous curvilinear capsulorhexis (CCC) technique of lens implantation has helped preserve a more natural position of the IOL and thus in the prediction of the post-operative ACD. Incremental improvements in IOL formulas, both theoretical and regression, have provided MAE approaching 0.5 D. However, an undesirable range of error is reported in various studies. In order to appreciate the limitations inherent in the prediction of resultant refractive error, one must understand the underlying sources of error in IOL calculations and their contributions to the final refractive error. Regardless of the accuracy of any predictive formula, the outcome still depends on measurement accuracy as well as the validity of IOL constants used in the calculation. The A-constant, surgeon factor, and ACD constant must be derived for each type of IOL. The use of inappropriate constants will introduce a systematic error in the refractive outcome. Regression analysis is commonly used to optimize existing formulas. In this manner, systematic errors can be corrected regardless of origin. The disadvantage of using actual post-operative refractive data in optimization of formulas or constants within formulas is the large sample size required to obtain statistical significance.

Aphakic IOL formulas include theoretical, empirical (usually derived from regression analysis), and combined formulas. The predictability of aphakic IOL formulas has improved incrementally over more than and has been evaluated in several publications.

The predictability of aphakic IOL formulas is limited primarily by the lack of pre-operative knowledge of the refractive effect that removal of the natural lens will have. This uncertainty is caused by the inability to measure the precise optical characteristics of the natural lens in the eye before surgery and to predict with certainty the optical certainty the optical changes that will occur upon lens removal, a feature not shared with phakic IOL formulas. Once a stable aphakic refraction is achieved, natural lens optics can be determined based on IOL power, thickness, shape characteristics and its precise location within the anterior segment of the eye. Surgically induced corneal shape changes must also be taken into account in this determination.

Despite surgical anatomical alterations, it is possible to predict aphakic IOL power with great accuracy. To this end, theoretical formulas include pre-operative average keratometry, axial length, anterior chamber depth, presumed location of the IOL within the anterior segment, and refractive indices of the cornea, aqueous and vitreous. Some formulas also introduce correction factors to adjust keratometry for assumed corneal index of refractive error. Error introduced by retinal thickness is also accounted for in some formulas. Finally, a surgeon factor can be added.

Holladay has provided a theoretical formula to predict refractive outcome for anterior chamber intraocular lenses that was applied to seven Baikoff anterior chamber lenses and three Momose anterior chamber intraocular lenses. The mean absolute prediction error was 0.42 D (standard deviation +/−0.60) and 0.57 D (standard deviation +/−0.64) respectively. Input data required by the Holladay formula include spectacle correction, vertex distance, and corneal curvature. In addition, an intraocular lens constant based on the location of the lens within the anterior chamber is required. The van der Heijde formula is similar, requiring manifest refraction adjusted for vertex distance, corneal curvature, and anterior chamber depth. As typically applied in the prior art, the van der Heijde model for predicting post-operative intraocular lens power (PIOL) is as follows:

$$PIOL = \frac{n}{N/(K + SE') - d} + \frac{n}{n/(K) - d}$$

where $n$ = 1.336 refractive index
$K$ = Mean central $K$ (keratometry)
$SE'$ = SE (spherical equivalent) at VD (Vertex distance) 0.0 mm
$d$ = ACD (anterior chamber depth) − 0.8 mm (Myopia)

When the van der Heijde model is used to predict the IOL power for Ophtec Artisan lenses implanted in multiple phakic eyes, the actual and residual IOL power data are shown in FIG. 9. These results show a root mean square error (Rsq) of 0.96 with a standard deviation (RMSE) of 0.5955. These data suggest that provide a consistently accurate result for a large number of patients when implanting intraocular lenses having a common physical configuration, an improved lens power prediction model is needed.

What is needed, then, is a method and model for allowing physicians and lens manufacturers to accurately and consistently predict the lens power needed for an intraocular lens used for the treatment of myopia in a specific patient so that when the patient is fitted with a lens that is manufactured with the predicted power, optimum refractive correction of the myopia is achieved.

SUMMARY OF THE INVENTION

The present invention provides improved predictability of the post-operative refraction using an intraocular lens (IOL), such as the Ophtec Artisan IOL, for correction of myopia in a phakic eye. Both pre-operative clinical measurement and the formula application are important for lens power calculations. Statistical regression analysis is applied to measurable pre-operative factors associated with each individual patient to determine which factors are most significant in accurately predicting the needed power in the intraocular lens ("PIOL"), how those factors should be weighted, and whether there are any interactions between factors that are predictive of lens power. After the factors and their weighting are determined, the treating physician obtains the data corresponding to those factors and supplies this data to the lens manufacturer for calculation of the PIOL. Alternatively, the physician can calculate the PIOL directly.

Therefore, the present invention includes a method of designing an intraocular lens for surgical implantation in a phakic eye, wherein the physician or lens manufacturer uses a first prediction model to make a prediction of lens powers for a plurality of test lenses having a common lens configuration, using a set of pre-operative factors for each of a corresponding number of myopic test patient eyes. The set of pre-operative factors are selected from a group of patient specific factors that can include pre-operative spherical equivalent (cycloplegic and/or manifest), vertex distance, anterior chamber depth, pre-operative average keratometry, desired post-operative spherical equivalent, and vertex distance. The physician or manufacturer then selects test lenses that will provide the predicted lens powers needed to provide the predicted post-operative refraction in the corresponding test patient eyes and surgically implants the test lenses. After the test eyes have stabilized, the physician obtains post-operative measurements of the actual post-operative refraction achieved in each of the test patient eyes. A multiple regression analysis of the actual post-operative measurements is performed as compared to the corresponding set of pre-operative measurements to identify and quantify which of the pre-operative factors have a statistically significant effect on accuracy of the predicted post-operative refraction. Then, using the identification and quantification of statistical significance determined by the multiple regression analysis, the first prediction model is modified to create a second prediction model. The physician/manufacturer obtains from the patient the pre-operative measurements selected from the group of patient factors as identified and used in the second lens power prediction model. Using the second lens power prediction model and pre-operative measurements obtained from the patient, the lens power is selected for the intraocular lens to be implanted in the patient. In a further embodiment of the invention, results from implantation of an IOL in a first eye of the patient can be used to further modify and enhance the prediction model for purposes of selecting the IOL power for the lens to be implanted in the patient's second eye.

In accordance with another aspect of the invention, a method of calculating a predicted lens power needed to provide a desired post-operative spherical equivalent to correct myopia in a phakic eye of a patient using an intraocular lens includes determining certain pre-operative characteristics of the eye, including cycloplegic and manifest spherical equivalent, vertex distance, anterior chamber depth, and keratometry, and then using each of the determined characteristics in a lens power prediction model to calculate the predicted lens power.

DETAILED DESCRIPTION OF THE PREFERRED EMBODIMENTS

Figure 1:
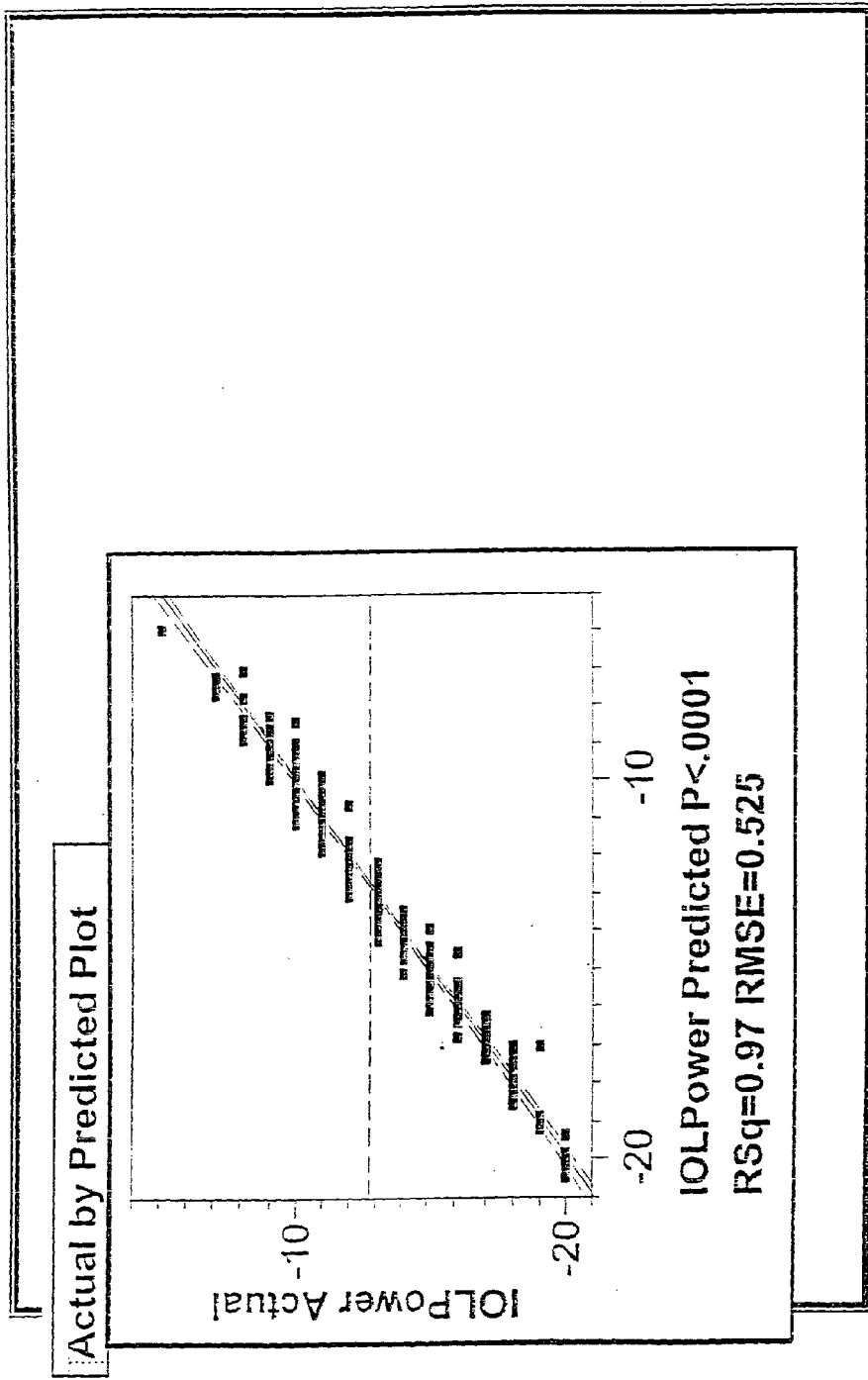
FIG. 1 is a graphical plot of actual intraocular lens (IOL) power versus predicted IOL power for 274 implanted intraocular lenses having a predicted lens power determined using a lens power prediction model developed in accordance with one embodiment of the invention.

Regression analysis is used by statisticians to study how the distribution of an output variable. In this this case, refraction varies in different groups of individuals. The groups of individuals are usually defined by one or more input variables. The output variable, of which there is only one in a particular regression analysis, is also called the criterion or predictand or outcome or dependent variable or regressand. The input variables are called predictors or independent variables or regressors or design variables.

In simple regression analysis, one input and one output variable are used, while in multiple regression there is one output variable, but more than one input variable. The important aspect is, however, the variation of the output as a function of the input. It is not that the output variable happens to be one-dimensional.

Because multiple regression analysis is an established statistical technique well known in the scientific community, the details of performing multiple regression analysis on a set of data will not be explained here in detail. Computer software exists that will allow a physician or IOL manufacturer to apply the methods of this invention to develop or use an accurate prediction model for the power of an IOL for implantation in a phakic eye of a patient. One example of such software is JMP 4.0.4 software available from the SAS Institute, Inc. Such software can be used to perform the multiple regression analysis called for in this invention on pre-and post operative data obtained by the physician from IOLs implanted in multiple patient eyes. Although such software includes instructions for use, the physician or manufacturer may desire to enlist the assistance of a statistician familiar with the software to perform the analysis and interpret the results, using patient factors identified by the methods of this invention.

Empirical regression formulas tend to find average keratometry and axial length to be important predictors. Additionally, measurement error, anterior chamber depth, and surgeon factor are combined into a single constant, e.g. the A constant. Regression formulas tend to be somewhat more predictive than theoretical formulas except when extremes of axial length are encountered. At these extremes, modern theoretical formulas tend to be more accurate.

In phakic IOL implant models, a different set of factors is needed as compared to prediction models used for other IOLs. In contrast to the aphakic situation, pre-operative refraction can be determined precisely because of lack of significant lens opacity. In addition, since the natural lens is not removed, the optical uncertainty this would create is eliminated. Thus, pre-operative refraction becomes a primary predictor of IOL power. Under these conditions, variations in the refractive state of eyes depend mainly on pre-operative keratometry, and on the optics of the natural lens including anterior chamber depth. Said differently, the pre-operative refraction can contain all of the predictive information contained in the keratometry and axial length. Therefore, to include keratometry and axial length, in addition to pre-operative refraction, would add nothing to phakic IOL predictability in some applications. In some applications, anterior chamber depth is important only as it predicts variation in the location of the phakic IOL within the anterior chamber. Therefore, the factors important in determining phakic IOL power can include weighted combinations and/or interactions of: (a) pre-operative refraction or spherical equivalent (cycloplegic and/or manifest and/or an average); (b) desired post-operative refraction or spherical equivalent (cycloplegic and/or manifest and/or an average); (c) anterior chamber depth from the corneal vertex to the anterior IOL surface (ACDIOL); (d) vertex distance; and (e) pre-operative average keratometry.

As a first step in developing a baseline prediction model, a conventional IOL prediction formula, such as the van der Heijde formula, can be used. The conventional model is used to predict the IOL powers needed to correct myopia in a set of phakic patient eyes ("test" eyes) using a series of test lenses having a common general physical configuration but having different PIOLs that are selected based on the conventional formula. In one embodiment of the invention, the Ophtec Artisan IOL is used. Pre-operative data are measured and tabulated for each test eye corresponding to multiple patient specific factors, including pre-operative refraction or spherical equivalent (cycloplegic and manifest), anterior chamber depth, vertex distance, and pre-operative keratometry. The desired post-operative refraction or spherical equivalent (cycloplegic and/or manifest and/or an average) is also tabulated. Each if the test lenses that have been selected according to the conventional prediction model are then implanted in the test eyes and the actual results (cycloplegic and manifest refraction or spherical equivalent) are measured as post-operative data.

Multiple regression analysis is then performed on the pre- and post-operative data to identify which factors are predictive of the actual IOL power needed to provide the desired post-operative refraction, to quantify the weighting coefficients that should be applied to each of the factors, and to identify any interactions between the factors. The results of this analysis are then used to derive a baseline prediction model for selection of PIOL for future IOLs of the same type. The accuracy and consistency (e.g., root mean square error and standard deviation) of the baseline model should also be compared the conventional prediction model to insure that improvement can be expected. The baseline prediction model can be further modified and refined, again using multiple regression analysis of patient factors using data obtained from implanting IOLs in additional phakic eyes, in which the PIOLs have been selected using the baseline model.

When the method of this invention was applied in one embodiment to an Artisan IOL from Ophtek, certain patient specific and other factors were found to have statistical significance in the accurate prediction of intraocular lens power required for optimum correction of myopia. Those factors were pre-operative cycloplegic and manifest spherical equivalent (Pre-CSE and MSE), vertex distance (VD—the distance between the inside surface of the cornea and the interior surface of the lens), post-operative goal CSE and MSE, anterior chamber depth (ACD), and pre-operative average keratometry (PreKAv). Conversely, also using the methods of this invention, other patient specific factors were found not to be statistically significant in the accurate prediction of IOL power. Those factors include AXL, the patient's age, the patient's gender, intraocular lens diameter, pupil size, and pre-operative cylinder CYL. In addition, the multiple regression analysis method of this invention was applied to the same data to determine the relative roles of pre- and post-operative CSE and MSE. Referring to Table 1 below, it was found that using an average or weighted average of the pre-operative cycloplegic and manifest SE (or refraction) (PreCMAv) provides optimum prediction of the needed intraocular lens power. Indeed, further analysis in accordance with the methods of this invention has demonstrated cycloplegic refraction and manifest refraction should be weighted 3:4 for some prediction models used with the Artisan IOL.

TABLE 1

FINDINGS
With Either Preop SE CYCLOPLEGIC or MANIFEST:

| | |
|---|---|
| ➤ Difference (Cyclo − Manifest) | p = 0.001 |
| ➤ Difference (Cyclo − Manifest)$^2$ | p = 0.001 |

Average (Cyclo + Manifest) × 0.5 Gives Best Prediction

Figure 2:
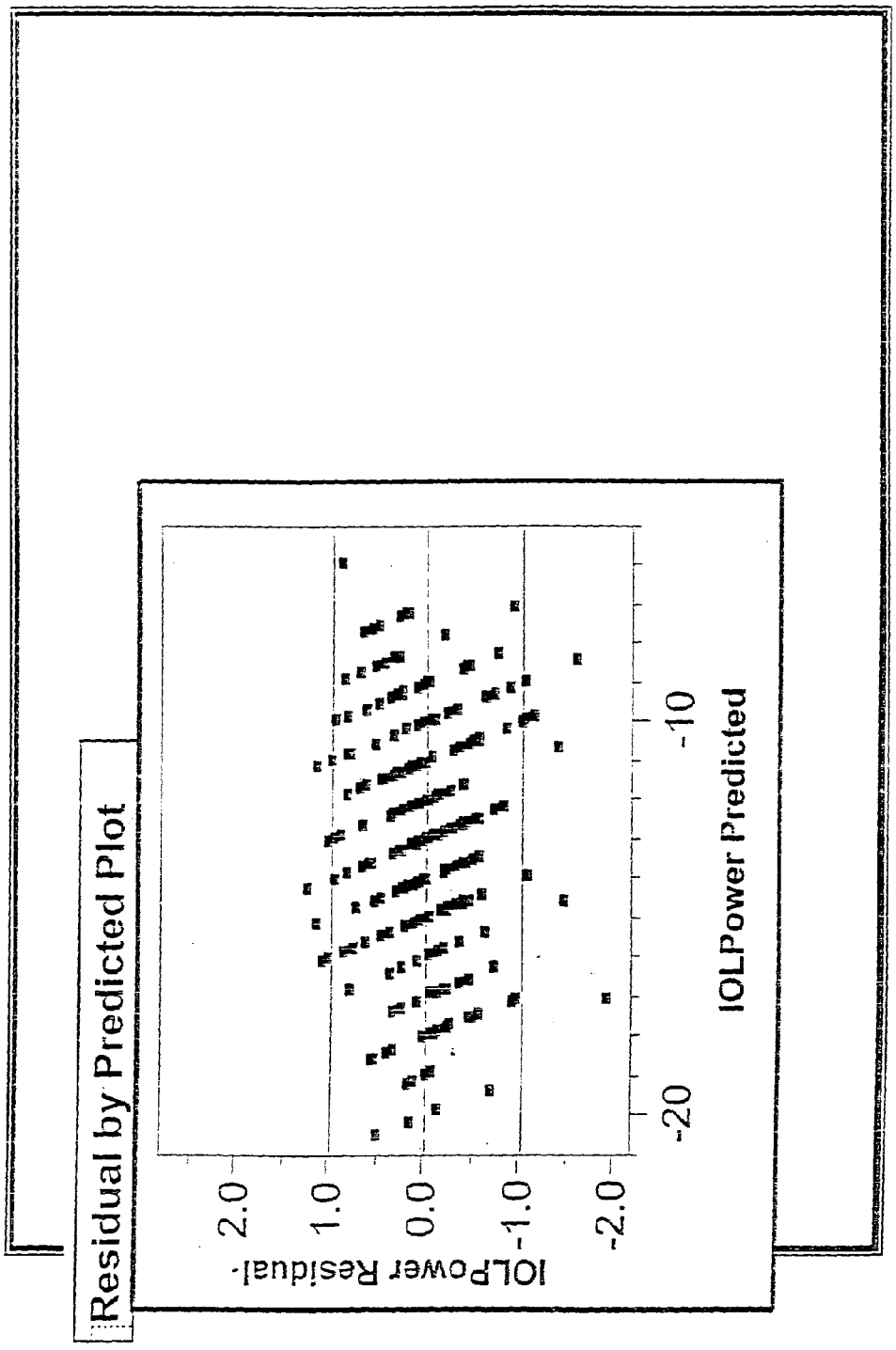
FIG. 2 is a graphical plot of residual IOL power versus predicted IOL power for the 274 intraocular lenses referenced in FIG. 1.
Figure 9:
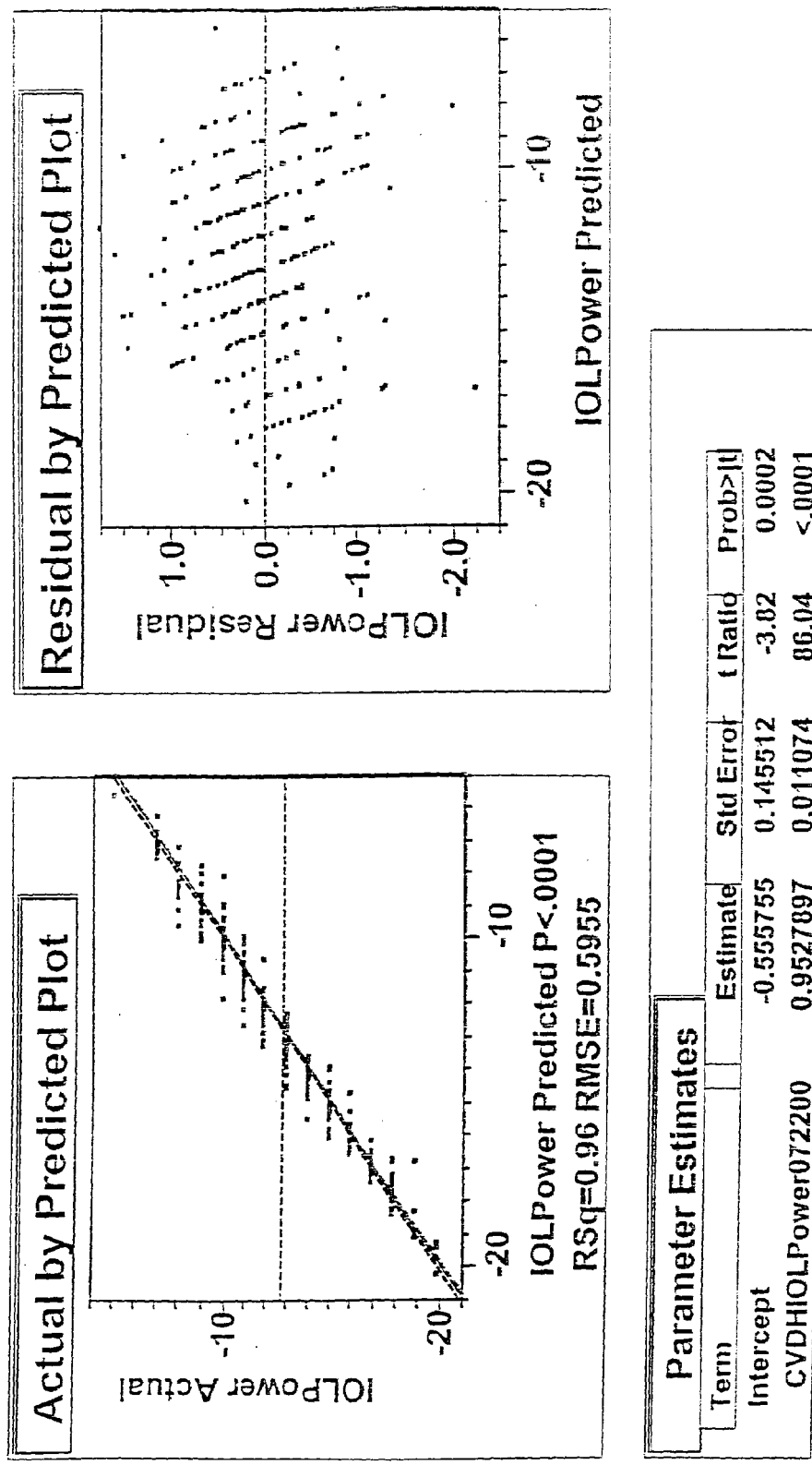
FIG. 9 contains graphical plots of actual and residual IOL power versus predicted IOL power for intraocular lenses used in eyes wherein the lens power prediction model is based on the Van der Heijde formula of the prior art.

FIG. 1 is a graphical plot of actual intraocular lens (IOL) power versus predicted IOL power for 274 implanted intraocular lenses having a predicted lens power determined using a baseline IOL power prediction model developed using the multiple regression analysis techniques as described above. FIG. 2 is a graphical plot of residual IOL power versus predicted IOL power for the 274 intraocular lenses referenced in FIG. 1. Note that the error (Rsq) and standard deviation (RMSE) results are improved as compared to the data reflected in FIG. 9 using a prior art prediction model.

Figure 3:
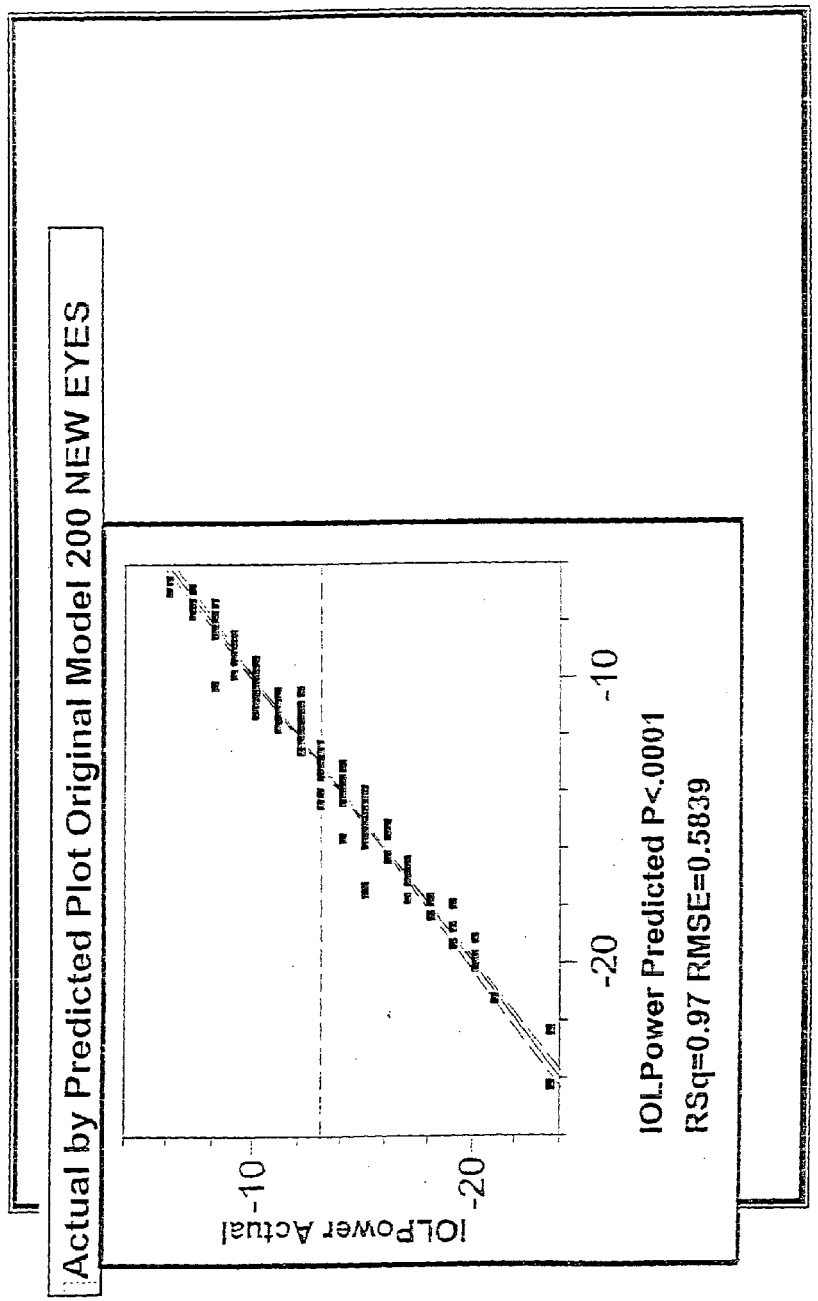
FIG. 3 is a graphical plot of actual IOL power versus predicted IOL power wherein the lens power prediction model as used in FIGS. 2 and 3 is applied prospectively to 200 new patient eyes.

The actual baseline prediction model as derived and used to generate the data shown in FIGS. 1 and 2 is shown in Table 2 below. Note that the prediction model includes the average of the manifest and cycloplegic post-operative SE (POCMAv) goals as a predictive factor. FIG. 3 is a graphical plot of actual IOL power versus predicted IOL power wherein the baseline power prediction model as used for FIGS. 2 and 3 is applied prospectively to 200 new patient eyes.

TABLE 2

Parameter Estimates

| Term | Estimate | Std Error | Prob > |t| |
|---|---|---|---|
| Intercept | 1.551039 | 1.029273 | 0.1331 |
| PreCMAv | 0.8422955 | 0.009243 | <.0001 |
| (PreCMAv + 12.5401)* (PreCMAv + 12.5401) | 0.0060066 | 0.002074 | 0.0041 |
| POCMAv | −0.277611 | 0.051842 | <.0001 |
| ACD | −0.666257 | 0.10772 | <.0001 |
| PreKAv | −0.03338 | 0.022267 | 0.1351 |

Figure 5:
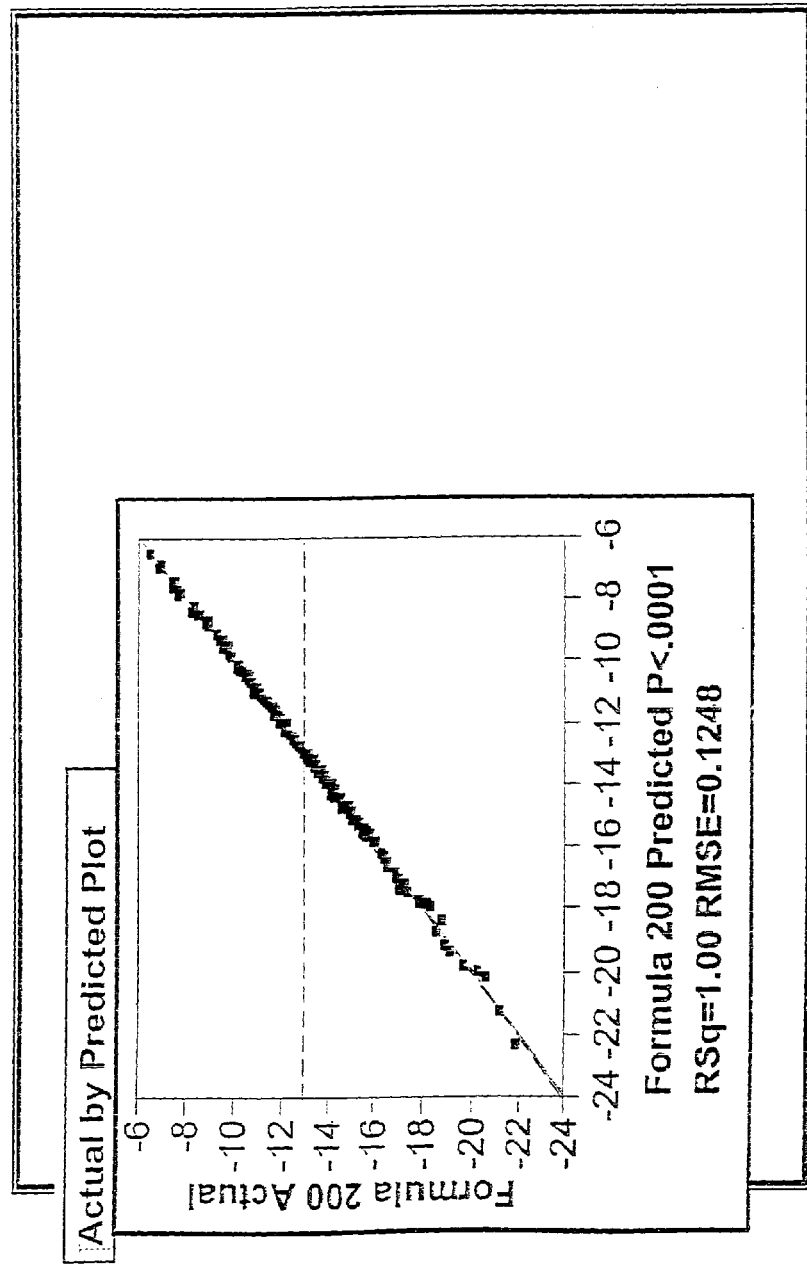
FIG. 5 is a graphical plot showing a comparison of actual vs. predicted IOL power using the prediction model of FIGS. 1 and 2 as compared to a modified prediction model using the method of the present invention and data from the 200 new patient eyes referenced in FIGS. 3 and 4.
Figure 6:
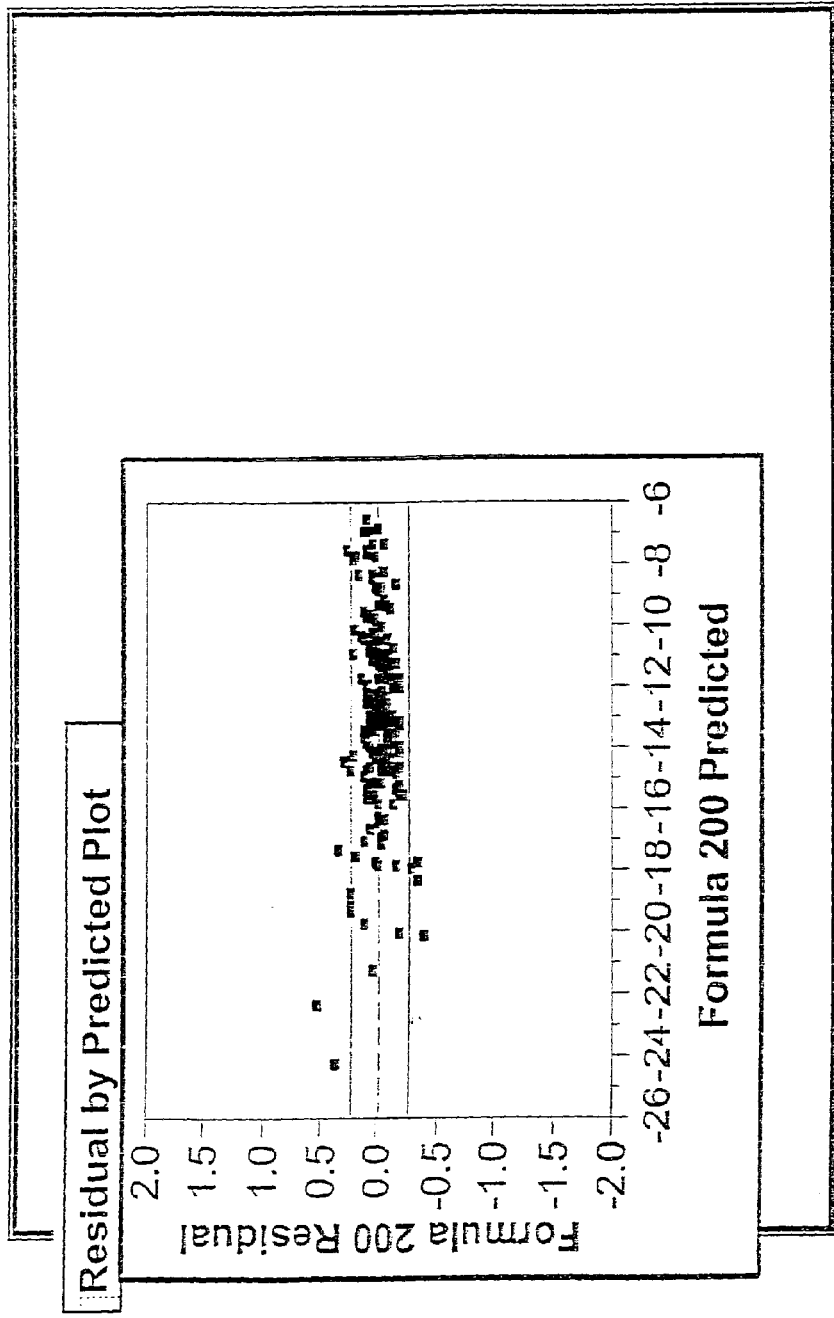
FIG. 6 is a graphical plot showing a comparison of residual vs. predicted IOL power using the prediction model of FIGS. 1 and 2 as compared to a modified prediction model using the method of the present invention and data from the 200 new patient eyes referenced in FIGS. 3 and 4.

The prediction model shown in Table 2 was modified and enhanced based on data from 200 new eyes, again using multiple regression analysis. The enhanced prediction model as derived is shown in Table 3, with plots of the results shown in FIGS. 4 and 5. Table 4 and FIG. 6 provide a statistical and graphical comparison between the baseline prediction model of Table 2 and FIGS. 1 and 2, as compared to a the enhanced prediction model as shown in Table 3, as reflected by the results shown in FIGS. 4 and 5.

TABLE 3

Parameter Estimates

| Term | Estimate | Std Error | Prob > |t| |
|---|---|---|---|
| Intercept | 2.5065603 | 1.151017 | 0.0306 |
| PreCMAv | 0.8398422 | 0.011974 | <.0001 |
| (PreCMAv + 12.7019)* (PreCMAv + 12.7019) | 0.0060764 | 0.001672 | 0.0004 |
| POCMAv | −0.425764 | 0.058724 | <.0001 |
| ACD | −0.669112 | 0.148374 | <.0001 |
| PreKAv | −0.058572 | 0.023757 | 0.0146 |

TABLE 4

Comparison of Baseline Model 274 with New Model 200

Summary of Fit

| | |
|---|---|
| RSquare | 0.998375 |
| Rsquare Adj | 0.998367 |
| Root Mean Square Error | 0.125965 |
| Mean of Response | −12.831 |
| Observations (or sum Wgts) | 200 |

Figure 4:
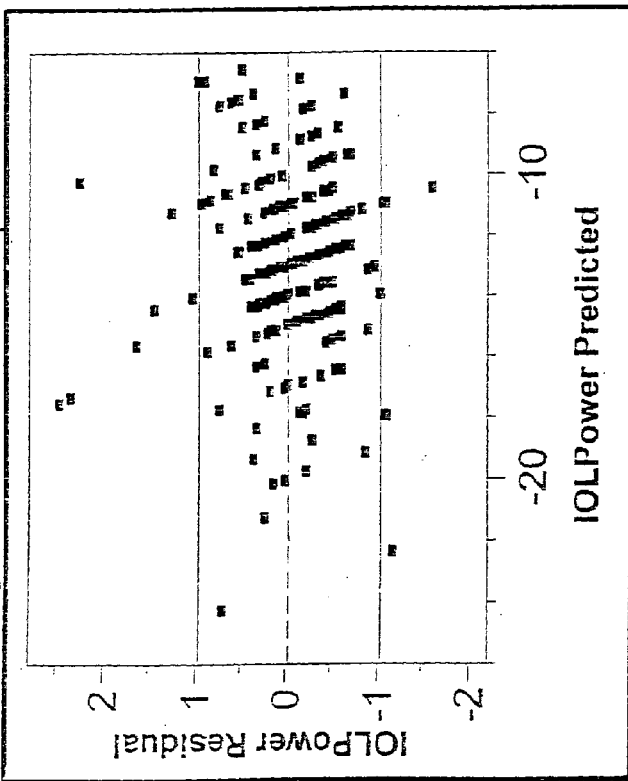
FIG. 4 is a graphical plot of residual IOL power versus predicted IOL power for the 200 new patient eyes referenced in FIG. 3.
Figure 7:
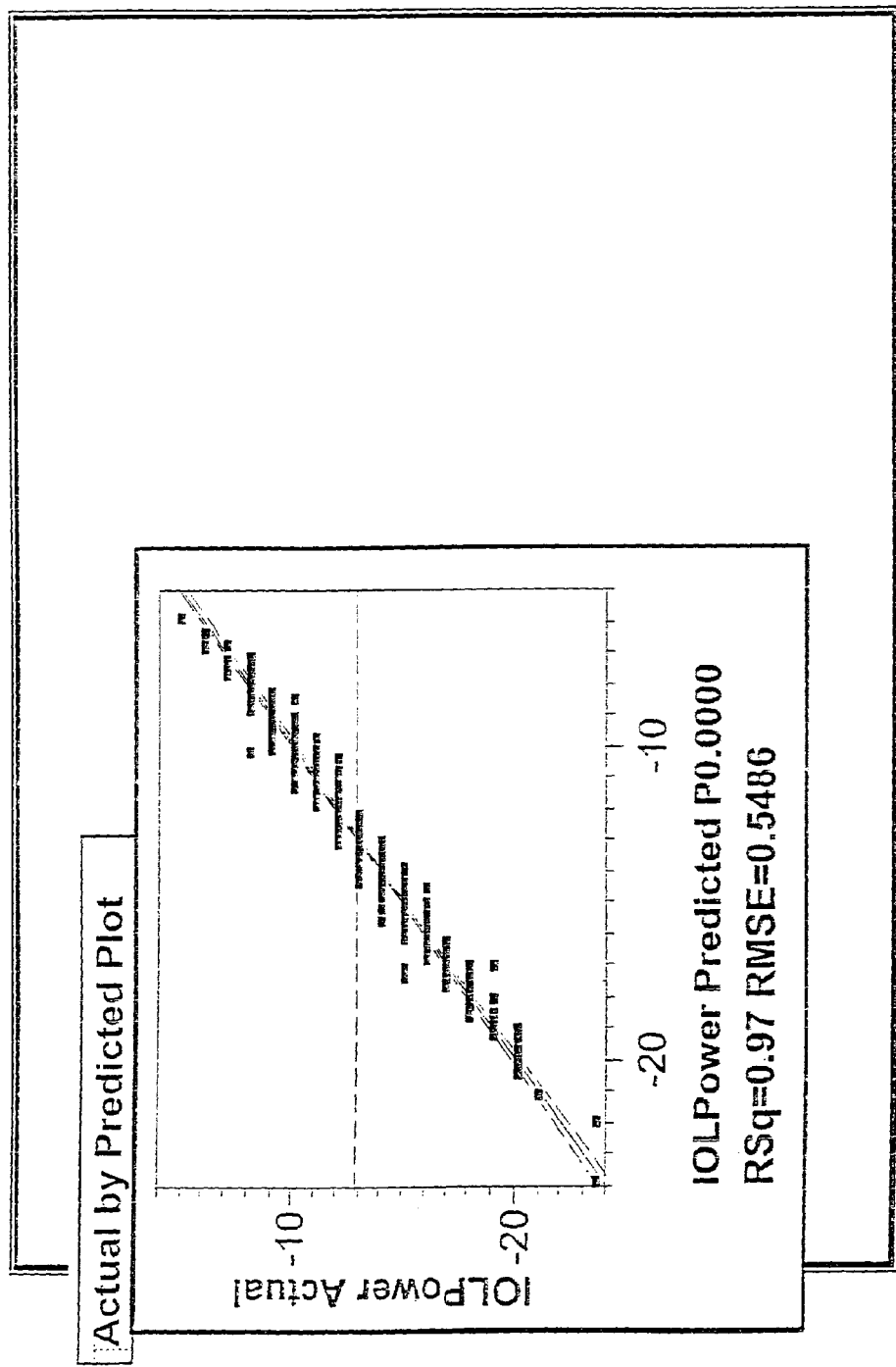
FIG. 7 is a graphical plot of actual IOL power versus predicted IOL power using one embodiment of the prediction model of this invention as applied to 474 patient eyes, combining the eyes referenced in FIGS. 1 and 2 with the eyes referenced in FIGS. 3 and 4.
Figure 8:
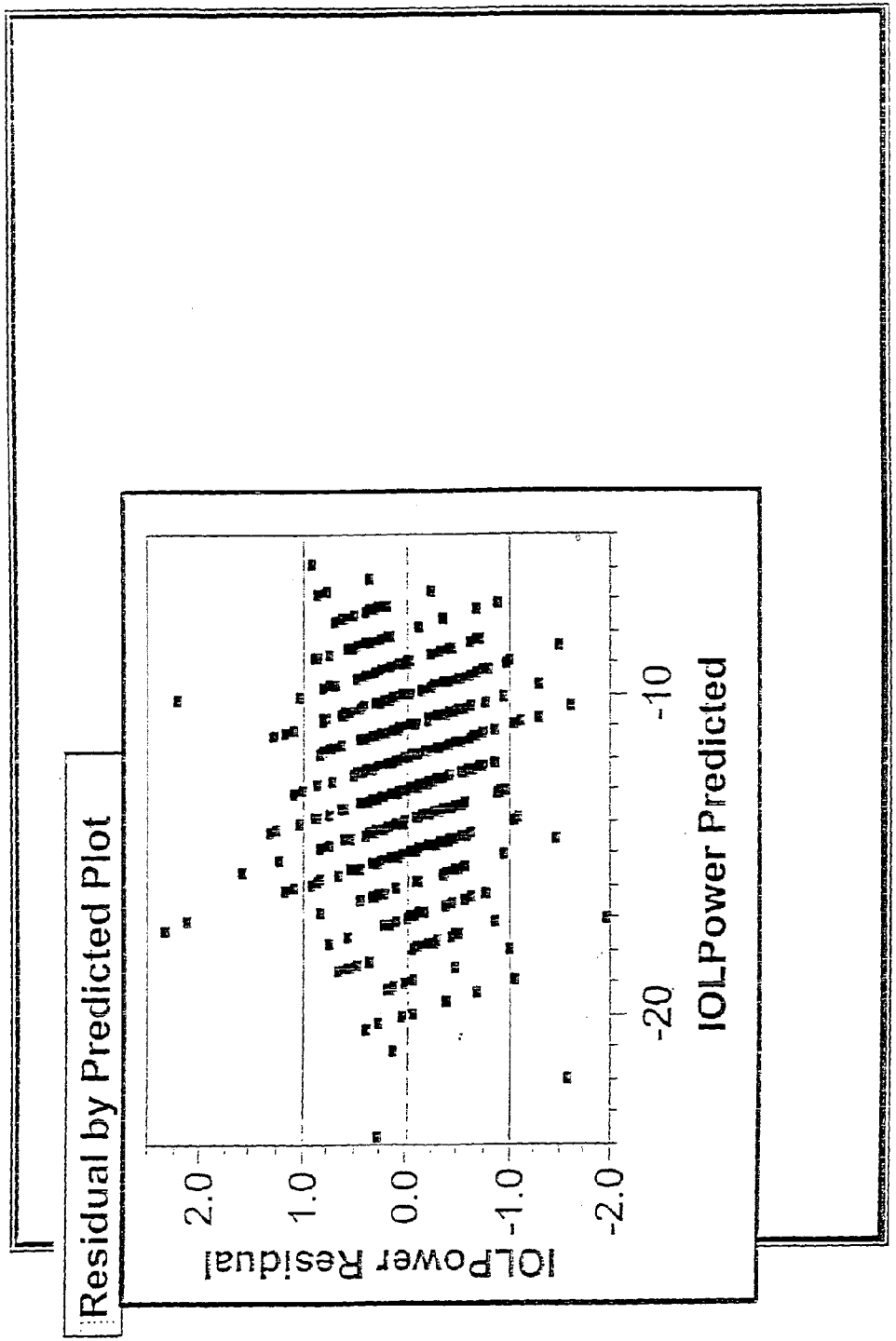
FIG. 8 is a graphical plot of residual IOL power versus predicted IOL power using one embodiment of the prediction model of this invention as applied to 474 patient eyes, combining the eyes referenced in FIGS. 1 and 2 with the eyes referenced in FIGS. 3 and 4.

FIG. 7 is a graphical plot of actual IOL power versus predicted IOL power using a further enhanced combined prediction model in accordance with the invention as applied to 474 patient eyes, combining the eyes referenced in FIGS. 1 and 2 with the eyes referenced in FIGS. 3 and 4. FIG. 8 is a graphical plot of residual IOL power versus predicted IOL power using the same combined model. Table 5 below summarizes the patient factors and corresponding coefficients used in the combined model, as derived by the multiple regression analysis method used in this invention.

TABLE 5

Parameter Estimates

| Term | Estimate | Std Error | Prob > |t| |
|---|---|---|---|
| Intercept | 1.83567 | 0.758455 | 0.0159 |
| PreCMAvg | 0.8401699 | 0.007339 | 0.0000 |
| (PreCMAvg + 12.6108)* (PreCMAvg + 12.6108) | 0.0068596 | 0.001204 | <.0001 |
| POCMAvg | −0.347509 | 0.037163 | <.0001 |
| ACD | −0.656183 | 0.087765 | <.0001 |
| PreKAv | −0.042884 | 0.01609 | 0.0080 |

Thus, a prediction model derived in accordance with one embodiment of this invention, for use with the Ophtec Artisan lens, and corresponding to the parameter estimates as specified in Table 5 above, can be stated as:

REGRESSION MODEL     Formula 1

1.8357

+0.8402 (*PreCMAv*)

+0.0069 (*PreCMAv* + 12.6108)$^2$

−0.3475 (*PCMAv*)

−0.6562 (*ACD*)

−0.0429 (*PreKAv*)

or as

REGRESSION MODEL     Formula 2

1.8357

+0.8402 (*PreCMAv*)

+0.0069 (*PreCMAv* + 12.6108)$^2$

−0.3475 (Desired *PO SE*)

−0.6562 (*ACD*)

−0.0429 (*PreKAv*)

where Desire PO SE is the desired post-operative spherical equivalent.

In yet a further enhancement of the prediction model, the results of IOL implantation in a patient's first eye ("First Eye Residual") is analyzed using multiple regression analysis and factored into the model as shown below:

REGISTRATION MODEL      Formula 3

$$1.8357$$
$$+0.8402\ (PreCMAv)$$
$$+0.0069\ (PreCMAv + 12.6108)^2$$
$$-0.3475\ (Desired\ PO\ SE)$$
$$-0.6562\ (ACD)$$
$$-0.0429\ (PreKAv)$$
$$+0.4752\ (First\ Eye\ Residual)$$

It should be noted that other factors can be considered or included in the model based on specific clinical needs. For example, a patient may benefit from having one eye having a different refraction from the second eye, so that a preferred compromise of near and farsightedness can be achieved. Also, in some applications the prediction model used for a specific patient may preferably include a variable adjustment factor based on ultrasound measurement of anterior chamber depth (ACD) or axial length (AXL), such that the quantity of the adjustment factor will vary depending on the value of a measured pre-operative factor.

It can be important in the derivation of prediction models in some applications to carefully consider the statistical significance of interactions between patient specific factors, even if regression analysis suggests that such factor in isolation is not predictive of IOL power. For example, analysis of data has suggested that interaction between ACD and PreCSE and between ACD and AXL can be predictive of IOL power.

In the first embodiment of the invention, the analysis uses only terms which contained a single variable. The single variable, PreCMAv, is created by averaging two fundamental measurements, PreCSE and PreMSE. Also, the variable, PreCMAv, was found to be a significant predictor of outcome in both its linear and quadratic form. All other significant variables were linear only. In a second embodiment, further analysis was conducted using the same dataset of 474 eyes as was analyzed previously resulting in the development of Formula 1. One purpose of further analyses was to determine whether the relationship between PreCSE and PreMSE might have even greater significance in an interactive form more complex than just the simple average of the these two variables. In addition, it was investigated whether there might be significant interactions among other variables that would enhance the predictability of the model.

Figure 10:
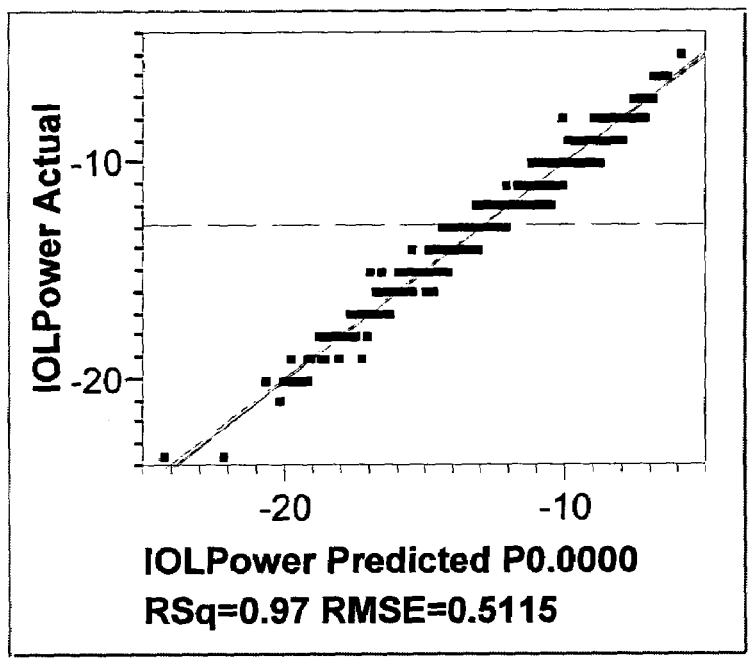
FIG. 10 is a graphical plot of actual IOL power versus predicted IOL power using a second embodiment of the prediction model of this invention as applied to 474 patient eyes, combining the eyes referenced in FIGS. 1 and 2 with the eyes referenced in FIGS. 3 and 4, using three variables not appreciated in the first embodiment of the invention: PreKStp, AXL, and Age.

FIG. 10 shows the results of analyses which investigate interactions among all variables. This model shows three variables not previously appreciated. These new variables are PreKStp, AXL, and Age. PreKStp is significant in its linear form and in interactions. AXL and Age are significant only as they interact with other variables. R-square is the portion of variation attributed to the model, between 0 and 1. Root Mean Squared Error "RMSE" estimates the standard deviation of the residual.

Figure 11:
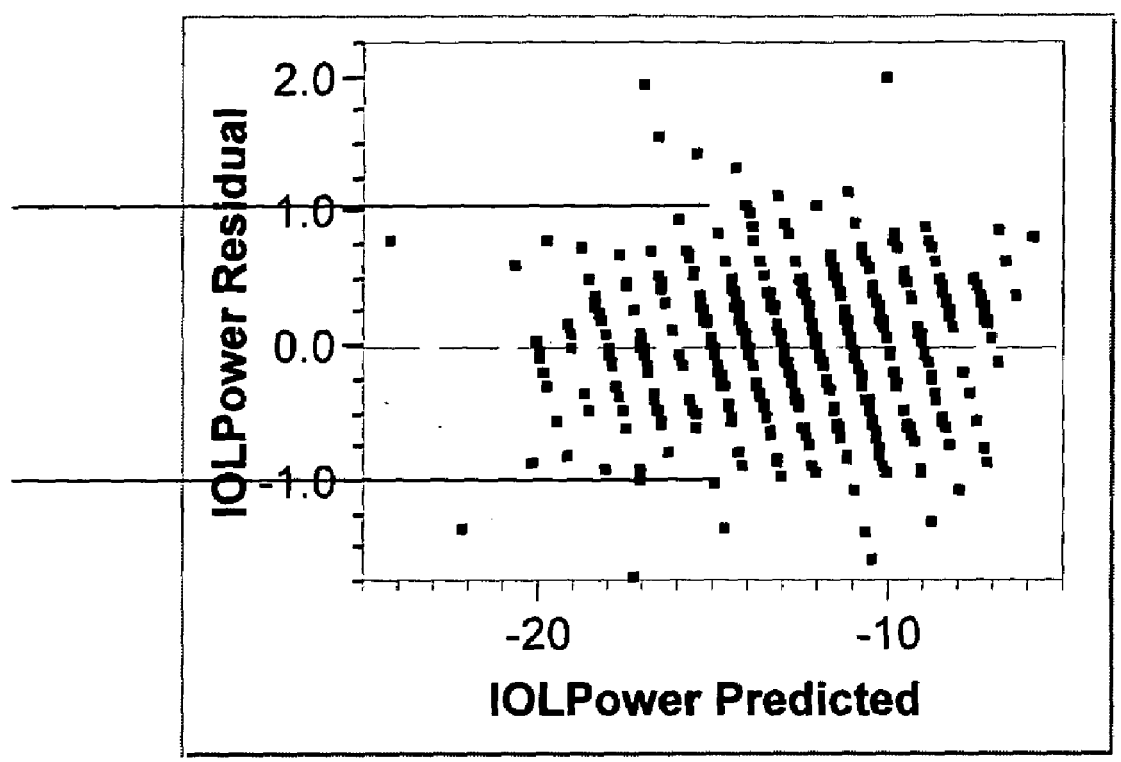
FIG. 11 is a graphical plot of residual IOL power versus predicted IOL power using the second embodiment of the prediction model of this invention as applied to 474 patient eyes, combining the eyes referenced in FIGS. 1 and 2 with the eyes referenced in FIGS. 3 and 4.

FIG. 11 is a graphical plot of residual IOL power versus predicted IOL power using the second embodiment of the prediction model of this invention as applied to 474 patient eyes, combining the eyes referenced in FIGS. 1 and 2 with the eyes referenced in FIGS. 3 and 4.

The new Interactive Model with interactions is more predictive than the Formula 1 model. The Interactive Model is found to have an RSquare value of 0.9733 whereas the Formula 1 model RSquare value is 0.9696. The Interactive Model has a smaller standard deviation, RMSE=0.5115 diopters, compared with Formula 1 model where RMSE=0.5486 diopters.

The actual baseline prediction model as derived and used to generate the data for the second embodiment is shown in Table 6 below

TABLE 6

Parameter Estimates

| Term | Estimate | Std Error | t Ratio | Prob > \|t\| |
|---|---|---|---|---|
| Intercept | 3.9546319 | 1.352333 | 2.92 | 0.0036 |
| PreMSE | 0.4001154 | 0.05118 | 7.82 | <.0001 |
| PreCSE | 0.4272423 | 0.051084 | 8.36 | <.0001 |
| (PreMSE + 12.6676)* (PreCSE + 12.5002) | −0.272308 | 0.087494 | −3.11 | 0.0020 |
| (PreCSE + 12.5002)* (PreCSE + 12.5002) | 0.1308234 | 0.044763 | 2.92 | 0.0037 |
| (PreMSE + 12.6676)* (PreMSE + 12.6676) | 0.1550405 | 0.045132 | 3.44 | 0.0006 |
| ACD | −0.73779 | 0.099135 | −7.44 | <.0001 |
| AXL | −0.042014 | 0.030176 | −1.39 | 0.1646 |
| (PreMSE + 12.6676)* (AXL − 27.6371) | 0.0843228 | 0.04155 | 2.03 | 0.0430 |
| (ACD − 3.66091)* (AXL − 27.6371) | 0.2638757 | 0.067334 | 3.92 | 0.0001 |
| (PreCSE + 12.5002)* (ACD − 3.66091) | 0.1063805 | 0.03255 | 3.27 | 0.0012 |
| (PreCSE + 12.5002)* (AXL − 27.6371) | −0.069771 | 0.041421 | −1.68 | 0.0928 |
| PreKStp2Adj | −0.065033 | 0.019386 | −3.35 | 0.0009 |
| POMSE | −0.104305 | 0.076471 | −1.36 | 0.1733 |
| POCSE | −0.280054 | 0.074965 | −3.74 | 0.0002 |
| (POMSE + 0.55111)* (POCSE + 0.41726) | 0.0674732 | 0.027751 | 2.43 | 0.0154 |
| Age | 0.0026627 | 0.003416 | 0.78 | 0.4361 |
| (Age − 39.4711)* (PreKStp2Adj − 45.4349) | 0.006974 | 0.001941 | 3.59 | 0.0004 |
| (PreCSE + 12.5002)* (ACD − 3.66091)* (AXL − 27.6371) | −0.027969 | 0.010688 | −2.62 | 0.0092 |

There is a predicted change in AveK (PredChgAveK) due to the surgical process, e.g., from the incision type (limbal, corneal or scleral), length and construction. Also any limbal relaxing incisions or astigmatic keratotomy would be expected to induce some change in corneal shape and, therefore, AveK. Such changes in AveK would usually be somewhat predictable preoperatively and could therefore be factored into the model. This hypothesis was tested using the data from one surgeon's (PNA) cases and demonstrate that a predicted AveK change should be introduced with a coefficient of 0.40. For second eye predictions, actual ChgAveK First Eye may be used, along with experience with similar surgeries, as predicted ChgAveK for second eye results.

As previously noted, First Eye Residual (see Formula 3) is a term which adds predictability to determination of second eye results. Therefore, First Eye Residual is added to Formula 4 also.

Therefore, the final formula is as follows:

$$3.9546 \quad \text{Formula 4}$$
$$+0.4001 * PreMSE$$
$$+0.4272 * PreCSE$$
$$+(PreMSE-(-12.6676))*((PreCSE-(-12.5002))*-0.2723)$$
$$+(PreCSE-(-12.5002))*((PreCSE-(-12.5002))*0.1308)$$
$$+(PreMSE-(-12.6676))*((PreMSE-(-12.6676))*0.155)$$
$$+-0.7378 * ACD$$
$$+-0.042 * AXL$$
$$+(PreMSE-(-12.6676))*((AXL-27.6371)*0.0843)$$
$$+(ACD-3.6609)*((AXL-27.6371)*0.2639)$$
$$+(PreCSE-(-12.5002))*((ACD-3.6609)*0.1064)$$
$$+(PreCSE-(-12.5002))*((AXL-27.6371)*-0.0698)$$
$$+-0.065 * PreKStp$$
$$+-0.1043 * -POMSE$$
$$+-0.2801 * POCSE$$
$$+(POMSE-(-0.5511))*((POCSE-(-0.4173))*0.0675)$$
$$+0.0027 * Age$$
$$+(Age-39.4711)*((PreKStp-45.4349)*0.007)$$
$$+(PreCSE-(-12.5002))*((ACD-3.6609)*((AXL-27.6371)*-0.028))$$
$$+0.4752 * \text{First Eye Residual}$$
$$+0.40 * PredChgAveK$$

Note that PreKStp2Adj is replaced in Formula 4 with the simplified name for this variable, PreKStp. PreKStp is the preoperative steeper central Keratometry measurement. AveK is the average of the two components of the central Keratometry measurement, i.e., the "Steep K" (greater of the pair of measurements) and the "Flat K" (lesser of the pair of measurements).

Note also that POMSE and POCSE would be assumed. POMSE represents the Desired Final Result or Desired PO SE. POCSE represents the expected POCSE primarily based on the preoperative PreMSE-PreCSE difference and other factors such as known spherical aberration. PredChgAveK is the preoperative Predicted Change in Average Keratometry based upon the surgeon's experience and knowledge of changes that usually occur in the corneal shape when using the corneal incisions he anticipates using in surgery.

A final note regarding further improvement in predicting IOL power: Further improvement likely will be made through the use of the actual measured corneal vertex to anterior iris plane dimension when this accurately can be done. This should provide greater predictability than use of corneal vertex to anterior lens dimension, ACD, since the anterior iris is the location of the attachment of the Artisan lens and since there is not an exact correlation between these two dimensions. For some lenses, such as a posterior chamber IOL which essentially floats on the anterior surface of the natural lens, the corneal vertex to anterior lens dimension, ACD, likely is the best IOL-Position variable.

Thus, although there have been described particular embodiments of the present invention of a new and useful Method for Determining Intraocular Lens Power for Correction of Myopia, it is not intended that such references be construed as limitations upon the scope of this invention except as set forth in the following claims.

What is claimed is:

1. A method of calculating a predicted lens power needed to provide a post-operative spherical equivalent to correct myopia in a phakic eye of a patient using an intraocular lens, the method comprising the steps of:
   a. measuring pre-operative and post-operative characteristics of the eye, including spherical equivalent, vertex distance, anterior chamber depth, keratometry, desired post-operative spherical equivalent, and first eye residual intraocular lens power; and
   b. using each of the measured pre-operative characteristics and desired post-operative characteristics in a lens power prediction model to calculate the predicted lens power; and
   c. wherein the lens power prediction model is a mathematical formula using the measured pre-operative and desired post-operative characteristics of the eye and corresponding coefficients substantially as follows $$3.9546$$
$$+0.4001 * PreMSE$$

-continued $+0.4272 * PreCSE$ $+(PreMSE - (-12.6676)) * ((PreCSE - (-12.5002)) * -0.2723)$ $+(PreCSE - (-12.5002)) * ((PreCSE - (-12.5002)) * 0.1308)$ $+(PreMSE - (-12.6676)) * ((PreMSE - (-12.6676)) * 0.155)$ $+ -0.7378 * ACD$ $+ -0.042 * AXL$ $+(PreMSE - (-12.6676)) * ((AXL - 27.6371) * 0.0843)$ $+(ACD - 3.6609) * ((AXL - 27.6371) * 0.2639)$ $+(PreCSE - (-12.5002)) * ((ACD - 3.6609) * 0.1064)$ $+(PreCSE - (-12.5002)) * ((AXL - 27.6371) * -0.0698)$ $+ -0.065 * PreKStp$ $+ -0.1043 * -POMSE$ $+ -0.2801 * POCSE$ $+(POMSE - (-0.5511)) * ((POCSE - (-0.4173)) * 0.0675)$ $+0.0027 * Age$ $+(Age - 39.4711) * ((PreKStp - 45.4349) * 0.007)$ $+(PreCSE - (-12.5002)) * ((ACD - 3.6609) * ((AXL - 27.6371) * -0.028))$ -continued $+0.4752 *$ First Eye Residual $+0.40 * PredChgAveK$ wherein PreCMAv is a weighted average of the pre-operative cycloplegic and manifest spherical equivalents (PreCSE and PreMSE), AXL is the axial length, POMSE is the desired post-operative manifest spherical equivalent, POCSE is the desired post-operative cycloplegic spherical equivalent, PreKStp is the preoperative steep keratometry measurement, PredChgAveK is the predicted change in average keratometry, ACD is the anterior chamber depth, PreKAv is the pre-operative average keratometry, and First Eye Residual is the residual intraocular lens power found after the first eye surgery.

\* \* \* \* \*